(12) United States Patent
Ramos Martín et al.

(10) Patent No.: US 9,708,282 B1
(45) Date of Patent: Jul. 18, 2017

(54) ANTI-INFLAMMATORY AND ANTIEPILEPTIC NEUROPROTECTIVE STATIN COMPOUNDS

(71) Applicant: NEURON BIOPHARMA, S.A., Armilla, Granada (ES)

(72) Inventors: Maria del Carmen Ramos Martín, Granada (ES); Fernando Guzmán Sánchez, Granada (ES); Soraya Santana Martínez, Granada (ES); Saleta Sierra Ávila, Granada (ES); Javier Santos Burgos Muñoz, Granada (ES)

(73) Assignee: NEURON BIOPHARMA, S.A., Armilla, Granada (ES)

( * ) Notice: Subject to any disclaimer, the term of this patent is extended or adjusted under 35 U.S.C. 154(b) by 0 days.

(21) Appl. No.: 14/896,315

(22) PCT Filed: Jun. 5, 2014

(86) PCT No.: PCT/ES2014/070463
§ 371 (c)(1),
(2) Date: Dec. 4, 2015

(87) PCT Pub. No.: WO2014/195553
PCT Pub. Date: Dec. 11, 2014

(30) Foreign Application Priority Data

Jun. 6, 2013 (ES) .................................. 201330844

(51) Int. Cl.
*C07D 309/30* (2006.01)
(52) U.S. Cl.
CPC ................... *C07D 309/30* (2013.01)
(58) Field of Classification Search
None
See application file for complete search history.

(56) References Cited

U.S. PATENT DOCUMENTS 6,541,511 B1    4/2003    Thaper

FOREIGN PATENT DOCUMENTS

EP    2 241 561 A1    10/2010
WO    99/11258 A1    3/1999

OTHER PUBLICATIONS

Askin, D. et al., "Synthesis of Synvinolin: Extremely High Conversion Alkylation of an ester Enolate," The Journal of Organic Chemistry, American Chemical Society, vol. 56, No. 16, Aug. 2, 1991, pp. 4929-4932.

International Search Report dated Nov. 20, 2014 for PCT/ES2014/070463.
Powell-Braxton, L. et al., "A mouse model of human familial hypercholesterolemia: markedly elevated low density lipoprotein cholesterol levels and severe atherosclerosis on a low-fat chow diet," Nat Med. 1998. 4: 934-938.
Ramirez, C. et al., "Simvastatin is the statin that most efficiently protects against kainate-induced excitotoxicity and memory impairment," J Alzheimers Dis. 2001. 24: 161-174.
Di, L., et al. "High throughput artificial membrane permeability assay for blood-brain barrier," Eur J Med Chem. 2003. 38 (3): 223-232.
Jick, H., et al. "Statins and the risk of dementia," Lancet. 2000. 356: 1627-1631.
Burgos, J.S. et al. "How statins could be evaluated successfully in clinical trials for Alzheimer's disease?" Am J Alzheimers Dis Other Demen. 2012. 27(3): 151-153.
Rishton GM, LaBonte K, Williams AJ, Kassam K, Kolovanov E. Computational approaches to the prediction of blood-brain barrier permeability: A comparative analysis of central nervous system drugs versus secretase inhibitors for Alzheimer's disease. 2006: 9 (3): 303-313.

*Primary Examiner* — Jeffrey S Lundgren
*Assistant Examiner* — Tori M Strong
(74) *Attorney, Agent, or Firm* — Knobbe, Martens, Olson & Bear, LLP

(57) ABSTRACT

A compound has formula (I), where R is selected from a methyl group or an ethyl group:

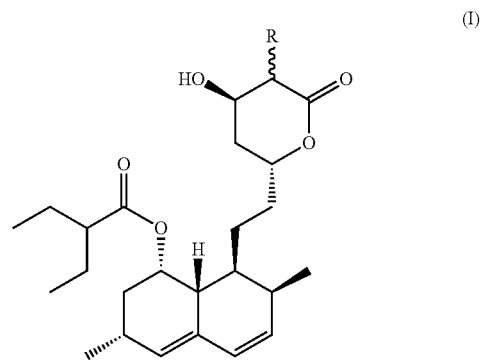

(I)

The compound can be hydroxy acid forms thereof, the pharmaceutically acceptable salts of the hydroxy acids and pharmaceutically acceptable prodrugs and solvates of the compounds and of the hydroxy acid forms thereof. The compounds can be used in the prevention or treatment of: neurodegenerative or neurological diseases, cognitive impairment, diseases with impaired APP metabolism, inflammation or inflammatory processes, or epilepsy, epileptic seizures and convulsions.

4 Claims, 10 Drawing Sheets

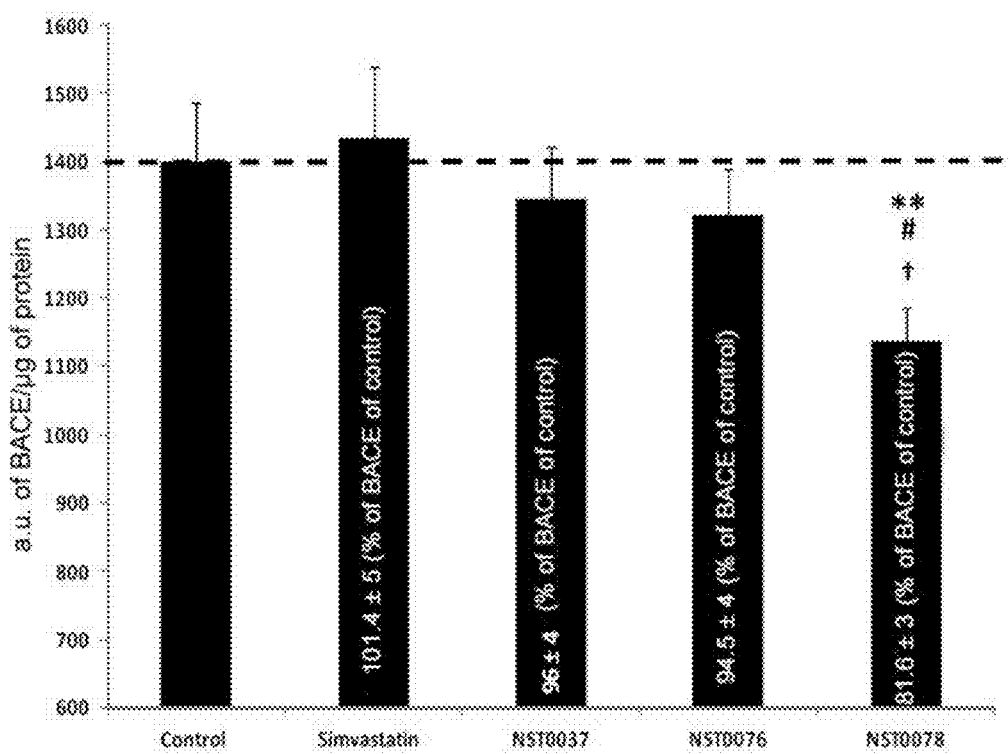

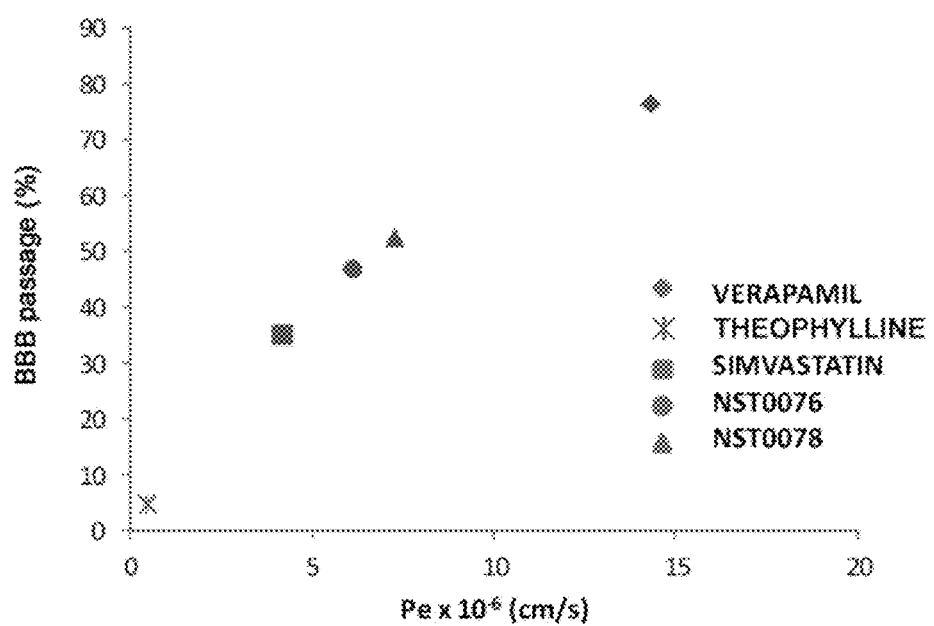

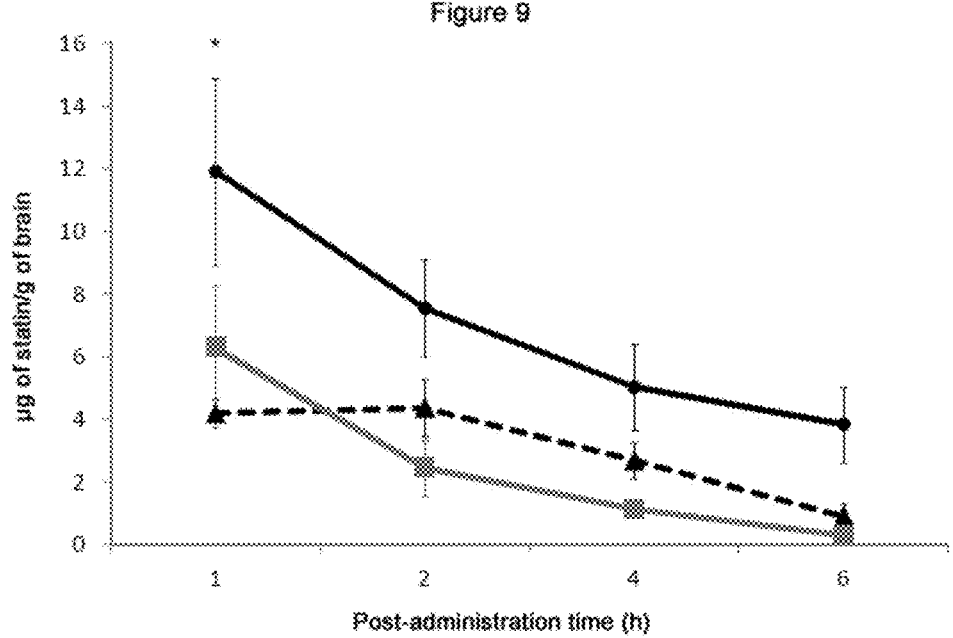

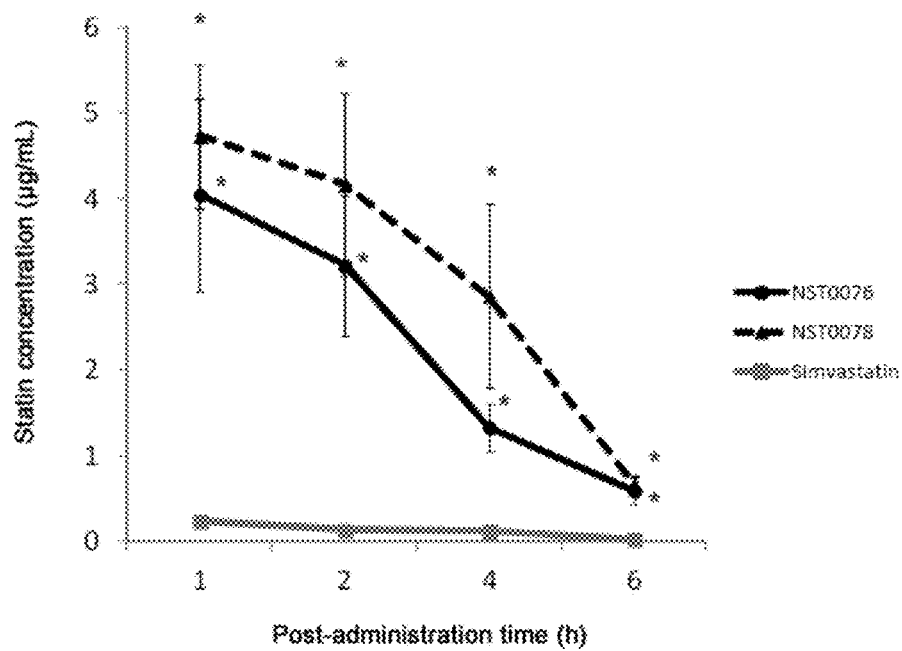

… …

ANTI-INFLAMMATORY AND ANTIEPILEPTIC NEUROPROTECTIVE STATIN COMPOUNDS

CROSS REFERENCE TO RELATED APPLICATIONS

This application is the U.S. National Phase of International Application No. PCT/ES2014/070463, filed Jun. 5, 2014, designating the U.S. and published in Spanish as WO 2014/195553 on Dec. 11, 2014 which claims the benefit of Spain Patent Application No. P201330844, filed Jun. 6, 2013. Any and all applications for which a foreign or domestic priority claim is identified here or in the Application Data Sheet as filed with the present application are hereby incorporated by reference under 37 CFR 1.57.

FIELD OF THE INVENTION

The present invention relates to the prevention and/or treatment of neurodegenerative or nervous system diseases, and particularly of Alzheimer's disease and epilepsy.

BACKGROUND OF THE INVENTION

The high incidence of neurodegenerative and/or neurological diseases is a problem of the first order worldwide. Therefore, it is necessary to search for neuroprotective compounds preventing or alleviating said diseases. Alzheimer's disease (AD) is the most prevalent among said diseases. Current drugs offer few benefits to patients, so it is necessary to search for neuroprotective compounds to alleviate this disease.

Since these drugs have had little success, new lines of research have opened up and, among them, research on inhibitors of 3-hydroxy-3-methylglutaryl-coenzyme A reductase (HMGCR) enzyme (better known as statins) as therapeutic agents stands out in recent years. In fact, a significant reduction of the risk of Alzheimer's has been described in patients treated with statins (Jick H, Zornberg G L, Jick S S, Seshadri 5, Drachman D A. Statins and the risk of dementia. Lancet. 2000. 356: 1627-1631). In the case of AD, several phase II clinical trials using mainly atorvastatin and simvastatin have been conducted in recent decades. However, up until now said studies were not capable of demonstrating the therapeutic efficacy of statins in Alzheimer's disease (Burgos J S, Benavides J, Douillet P, Velasco J, Valdivieso F. How statins could be evaluated successfully in clinical trials for Alzheimer's disease? Am J Alzheimers Dis Other Demen. 2012. 27(3): 151-153).

It is known in the state of the art (EP2241561) that modifications in the hexahydronaphthalene ring structure of certain statins results in statins (NST0037) with a high hypocholesterolemic and neuroprotective capacity. It had been previously identified that methylation in the β-hydroxypyranone ring in simvastatin produced a derivative with in vitro HMGCR inhibitory capacity which translated into an in vivo hypocholesterolemic effect (U.S. Pat. No. 6,541,511 B1), although this document does not refer to the neuroprotective capacity of said modified statin.

There is a need today to develop new compounds, particularly statins, with therapeutic efficacy in neurodegenerative diseases, i.e., compounds with high neuroprotective activity which additionally have a good blood-brain barrier passage.

SUMMARY

The present invention describe two new derivatives of statin NST0037 where the β-hydroxypyranone ring of the molecule has been protected by means of incorporating a methyl group or an ethyl group. These new derivatives are (1S, 3R, 7S, 8S, 8aR)-8-(2-((2R, 4R)-4-hydroxy-5-methyl-6-oxotetrahydro-2H-pyran-2-yl)ethyl)-3,7-dimethyl-1,2,3,7,8,8a-hexahydronaphthalen-1-yl 2-ethylbutanoate (also sometimes identified as NST0076 in this patent application) and (1S, 3R, 7S, 8S, 8aR)-8-(2-((2R,4R)-5-ethyl-4-hydroxy-6-oxotetrahydro-2H-pyran-2-yl)ethyl)-3,7-dimethyl-1,2,3,7,8,8a-hexahydronaphthalen-1-yl 2-ethylbutanoate (also sometimes identified as NST0078 in this patent application). According to in vitro and in vivo assays performed by the inventors, in comparison with what is described in U.S. Pat. No. 6,541,511 B1, these modifications surprisingly did not produce molecules with HMGCR inhibitory activity similar to or better than the starting molecule. However, and also surprisingly, the inventors detected high neuroprotective capacity of the two molecules NST0076 and NST0078 of the invention. In fact, the compounds of the invention have great in vivo neuroprotective potential surpassing that of simvastatin, further protecting against epilepsy, reducing β-secretase (BACE) enzymatic activity, which is a therapeutic target for treatment of AD as it is responsible for the amyloidogenic pathway in amyloid precursor protein (APP) processing, and reducing neuroinflammation. Additionally, the inventors decided to study the blood-brain barrier (BBB) passage of derivatives NST0076 and NST0078, with the surprising finding that levels of both compounds in the brain are much higher than those detected for simvastatin, which was confirmed with in vitro assays which also predicted improved brain access.

The absence of hypolipidemic activity in the compounds was clearly shown by means of determining the activity of said compounds on HMGCR in comparison with a commercial statin inhibiting the enzyme (simvastatin) and with monacolin J, which has a similar structure but with an HMGCR inhibitory capacity much less than that of simvastatin (Example 2, FIG. 1). In order to better characterize the effects of the compounds on lipid metabolism and compare the results obtained in vitro, the inventors decided to analyze hypocholesterolemic activity in more detail by using in vivo models and evaluating the acute effect of the derivative compounds NST0076 and NST0078 in a familial hyperlipidemia model in mice (Example 2, FIG. 2).

The antiepileptic and anticonvulsant activity of the compounds has been demonstrated by means of determining protection against epileptic seizures and convulsions in an epilepsy model in mice (Example 3, FIG. 3). Said example clearly shows the potential use of these compounds in the prevention and/or treatment of epilepsy and epileptic seizures or convulsions. The neuroprotective effect of NST0076 and NST0078 has been evaluated with respect to hippocampal neuronal damage caused by the action of an excitotoxic substance (Example 3, FIGS. 4 and 5). The inventors found that these compounds are surprisingly better neuroprotectors than simvastatin, protecting against neuronal death and induced neuroinflammation. Said example clearly shows the potential use of these compounds in the prevention and/or treatment of diseases associated with excitotoxic syndrome, such as neurodegenerative and/or neurological diseases.

The effect of the compounds on β-secretase (BACE) activity has also been evaluated, surprisingly observing that compounds NST0076 and NST0078, unlike simvastatine, have an inhibitory effect on BACE in the brain of rodents or zebra fish (Example 4, FIGS. 6 and 7). Said example clearly shows the potential use of this compound in the prevention and/or treatment of diseases associated with impaired β-amyloid precursor protein (APP) metabolism, such as AD.

For the purpose of defining the blood-brain barrier passage of compounds NST0076 and NST0078, different parameters, such as theoretical barrier passage determined by compound lipophilicity, have been analyzed in silico or by means of in vitro assays, analyzing the percentage of BBB passage and the effective permeability thereof (FIG. 8) as described in Example 5, where it is observed that both NST0037 derivatives have a high theoretical BBB passage, such passage being surprisingly higher than that of simvastatin. Additionally, it was verified in mice that the molecules surprisingly have greater access to the brain in the case of new NST0037 derivatives with respect to the passage of a reference statin, i.e., simvastatin (Example 5, FIG. 9). Plasma concentrations of these molecules with respect to simvastatin have been subsequently determined (Example 5, FIG. 10), very high and statistically significant concentrations of NST0076 and NST0078 surprisingly being observed with respect to simvastatin.

Therefore, one aspect of the present invention relates to two compounds of formula (I), where R is selected from a methyl group [also sometimes identified as NST0076 in this patent application] and an ethyl group [also sometimes identified as NST0078 in this patent application]:

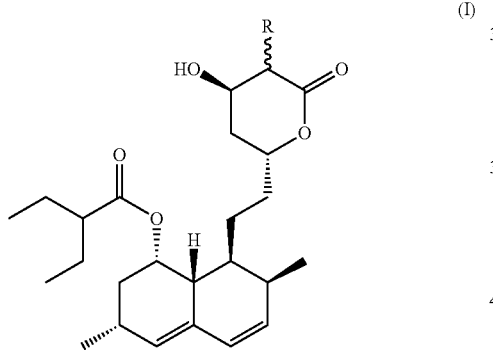

(I)

to the hydroxy acid forms thereof, to the pharmaceutically acceptable salts of said hydroxy acids and to pharmaceutically acceptable prodrugs and solvates of the compound and of the hydroxy acid forms thereof.

Another aspect of the present invention is a pharmaceutical composition comprising compounds of formula (I) and/or the hydroxy acid forms thereof and/or a pharmaceutically acceptable salt of said hydroxy acids and/or a pharmaceutically acceptable prodrug or solvate of the compounds or of the hydroxy acid forms thereof, and at least one pharmaceutically acceptable adjuvant, carrier and/or vehicle.

Another aspect of the present invention relates to compounds of formula (I), to the hydroxy acid forms thereof or a pharmaceutically acceptable salt of said hydroxy acids and/or to a pharmaceutically acceptable prodrug or solvate of the compounds or of the hydroxy acid forms thereof for use as a medicinal product.

According to another aspect, the present invention relates to an ethylated derivative and a methylated derivative of the compound of formula (I), to the hydroxy acid forms thereof or to a pharmaceutically acceptable salt of said hydroxy acids and/or to a pharmaceutically acceptable prodrug or solvate of the compounds or of the hydroxy acid form thereof for use as a neuroprotective agent, particularly in the prevention and/or treatment of:

a. neurodegenerative or nervous system diseases (e.g., Alzheimer's disease, Huntington's disease, Parkinson's disease, amyotrophic lateral sclerosis (ALS) or multiple sclerosis, Creutzfeldt-Jakob, Friedreich's ataxia, Lewy body dementia, spinal muscular atrophy, spongiform encephalopathies, Devic's disease, Guillain-Barré syndrome, Canavan disease, spondylosis, Lafora disease, Down syndrome, Korsakoff's syndrome, etc.), more specifically as neuroprotective agent against APP metabolism impairments associated with said chronic neurodegenerative diseases,
b. cognitive impairment,
c. inflammation or inflammatory processes, and
d. epilepsy, status epilepticus, epileptic seizures and convulsions.

One aspect of the present invention relates to the use of compounds of formula (I), of the hydroxy acid forms thereof, of a pharmaceutically acceptable salt of said hydroxy acids and/or of a pharmaceutically acceptable prodrug or solvate of the compounds or of the hydroxy acid forms thereof in the preparation of a medicinal product. According to a particular embodiment, the medicinal products are for use as neuroprotective agents, particularly in the prevention and/or treatment of:

a. neurodegenerative or nervous system diseases (e.g., Alzheimer's disease, Huntington's disease, Parkinson's disease, amyotrophic lateral sclerosis (ALS) or multiple sclerosis, Creutzfeldt-Jakob, Friedreich's ataxia, Lewy body dementia, spinal muscular atrophy, spongiform encephalopathies, Devic's disease, Guillain-Barré syndrome, Canavan disease, spondylosis, Lafora disease, Down syndrome, Korsakoff's syndrome, etc.), more specifically for protection against impaired APP metabolism associated with said chronic neurodegenerative diseases,
b. cognitive impairment,
c. Inflammation or inflammatory processes, and
d. epilepsy, status epilepticus, epileptic seizures and convulsions.

In another aspect, the invention relates to a method for the prevention and/or treatment of neurodegenerative or nervous system diseases, cognitive impairment, epilepsy, epileptic seizures and convulsions, or diseases associated with impaired APP metabolism, in a subject in need of treatment, which comprises administering to said subject a therapeutically effective amount of compounds of formula (I), the hydroxy acid forms thereof or a pharmaceutically acceptable salt of said hydroxy acids and/or a pharmaceutically acceptable prodrug or solvate of the compounds or of the hydroxy acid forms thereof.

BRIEF DESCRIPTION OF THE DRAWINGS

FIG. 3 is a bar graph depicting the mean±SEM of the percentage of the area under the curve of the epilepsy levels with respect to the Vehicle+KA group, shown by the mice during 120 minutes of observation after the inoculation of kainate (23 mg/kg) according to the pretreatment received. Pretreatments (n=12, Simvastatin+KA group), NST0076 (n=10, NST0076+KA group) and NST0078 (n=10, NST0078+KA group) were administered i.p. at 3.125 mg/kg 24 h and 0.5 h before inducing damage with kainate. The control mice received equivalent volumes of the vehicle (0.5% methylcellulose in saline solution) with the same regimen (n=10, Vehicle+KA group). *p-value<0.05 with respect to the Vehicle+KA group (Student's t-test).

FIG. 4 is a stacked bar graph depicting the percentage of dead animals, the percentage of animals with hippocampal damage and the percentage of animals without damage in said region according to the treatment administered. The experiment consisted of five experimental groups: Vehicle+PBS+Vehicle group (n=9), Vehicle+KA+Vehicle group (n=20), Simvastatin+KA+Simvastatin group (n=12), NST0076+KA+NST0076 group (n=10), and NST0078+KA+NST0078 group (n=10). The mice were pretreated i.p. with a dose of 3.125 mg/kg 0.5 h and 24 h before inducing damage by means of inoculating kainate (23 mg/kg). The group of mice that was not treated with kainate received PBS instead. The mice continued to be treated (1 dose/day) three days after the administration of kainate. Mice from the vehicle groups received equivalent volumes of 0.5% methylcellulose in saline solution. On the fourth day, the surviving animals were sacrificed and their brains were extracted and processed for preparing 5 μm coronal sections, which were then stained with hematoxylin and eosin. The brains were analyzed, recording the damage detected in the hippocampus. The number of times the percentage of the recorded data exceeds that of the Simvastatin+KA+Simvastatin group is indicated in each case.

FIG. 5 is a bar graph depicting the degree to which astrogliosis has spread (or score) in the different areas of the brain affected by kainate according to treatment, being expressed as the mean±SEM of the score recorded in the brains of surviving animals. The experiment consisted of five experimental groups: Vehicle+PBS+Vehicle group (n=9), Vehicle+KA+Vehicle group (n=20), Simvastatin+KA+Simvastatin group (n=12), NST0076+KA+NST0076 group (n=10) and NST0078+KA+NST0078 group (n=10). The mice were pre-treated i.p. with a dose of 3.125 mg/kg 0.5 h and 24 h before inducing damage by means of inoculating kainate (23 mg/kg). The group of mice that was not treated with kainate received PBS instead. The mice continued to be treated (1 dose/day) three days after the administration of kainate. The mice from the vehicle groups received equivalent volumes of 0.5% methylcellulose in saline solution. On the fourth day, the surviving animals were sacrificed and their brains were extracted and processed for preparing 5 μm coronal sections, which were then stained for the GFAP protein present in the astroglia. The brains were analyzed by recording the spread of astrogliosis (in the score, zero indicates the absence of reactive astroglia and three indicates maximum reactive astroglia). *p<0.05 with respect to the vehicle+KA+vehicle group (Student's t-test).

FIG. 7 is a bar graph depicting the mean±SEM of β-secretase (BACE) enzymatic activity in the brain of zebra fish 24 h after i.p. administration of 100 mg/kg of a suspension of simvastatin, NST0076, NST0078 or of the equivalent volume of the vehicle thereof (0.5% methylcellulose in saline solution) to adult zebra fish 24 months of age. Enzymatic activity was determined in vitro in brain homogenates by means of using a fluorogenic substrate and was expressed in arbitrary units of the enzyme normalized by the amount of protein (determined by means of the BCA method). **p<0.01 with respect to the control group; #p<0.05 with respect to the Simvastatin group (Student's t-test test).

FIG. 8 is an XY scatter plot depicting the effective permeability expressed as $P_e$ (cm/s) with respect to blood-brain barrier (BBB) passage (%) of simvastatin, NST0076 and NST0078 in the hydroxy acid forms thereof. Both parameters were determined in vitro by means of the PAMPA (Parallel Artificial Membrane Permeability Assay) method. Verapamil and theophylline were used as positive and negative controls respectively.

FIG. 9 is an XY scatter plot depicting the concentration of the lactone forms of simvastatin, NST0076 and NST0078 in the brain 1, 2, 4 and 6 h after i.p. administration of a suspension of the compounds at 50 mg/kg to male FVB mice (n=4-8/group/time) using 0.5% methylcellulose in saline solution as a vehicle. The concentrations of the compounds were determined by means of UPLC-MS. The results are the mean±SEM of the determined concentrations expressed per amount of brain. * Significant difference with respect to the Simvastatin group, according to Student's t-test (p<0.05). The Cmax, tmax and $AUC_{0-6}$ (Area Under the Curve) values were calculated based on each group of animals.

FIG. 10 is an XY scatter plot depicting the concentration of the lactone forms of simvastatin, NST0076 and NST0078 in plasma 1, 2, 4 and 6 h after i.p. administration of a suspension of the compounds at 50 mg/kg to male FVB mice (n=4-8/group/time) using 0.5% methylcellulose in physiological saline as a vehicle. The concentrations of the compounds were determined by means of UPLC-MS. The results are the mean±SEM of the determined concentrations expressed in μg/mL. * Significant difference with respect to the simvastatin group, according to Student's t-test (p<0.05). The Cmax, tmax and $AUC_{0-6}$ (Area Under the Curve) values were calculated based on each group of animals.

DETAILED DESCRIPTION OF CERTAIN EMBODIMENTS OF THE INVENTION

Definitions

Figure 1:
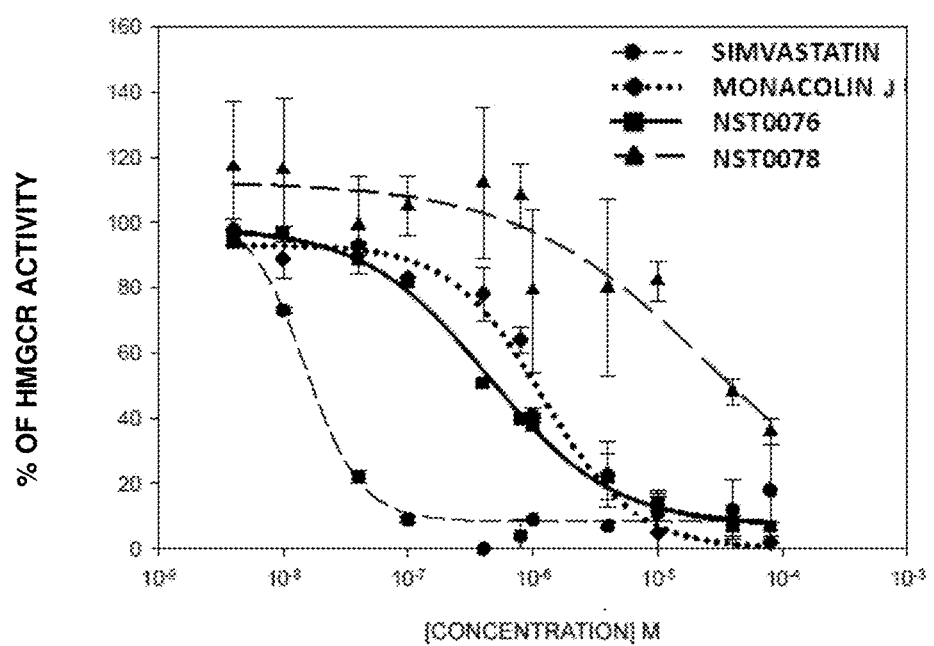
FIG. 1 is an XY scatter plot depicting inhibition of 3-hydroxy-3-methylglutaryl coenzyme A reductase (HMGCR) enzyme activity by the compounds NST0076, NST0078, monacolin J and simvastatin in their hydroxy acid forms. The figure shows the percentage of HMGCR enzyme activity after treatment with the compounds at different concentrations, depicting the means±SD of one experiment in duplicate. A table summarizing the $IC_{50}$ (concentration at which 50% of the enzyme activity is inhibited) results for the four compounds is shown.

To aid in understanding the invention object of this patent application, the meaning of some terms and expressions used in the context of the invention is described below.

As it is used herein, the term "neuroprotective" refers to any substance capable of causing the attenuation disappearance of the effects of neuronal degeneration or death by means of any mechanism known or to be known, for example, necrosis, apoptosis, autophagia, oxidative damage, excitotoxicity, endoplasmic reticulum damage, byproduct deposition, cytoskeleton disorganization, electron transport chain inhibition, loss of cell architecture, protein hyperphosphorylation or dephosphorylation, etc, or to the reduction or disappearance of side effects As it is used herein, the term "statin" refers to an inhibitor of the 3-hydroxy-3-methylglutaryl-coenzyme A reductase (HMGCR) enzyme, which catalyzes the limiting step of cholesterol biosynthesis and includes any natural, synthetic or semi-synthetic statin. However, compounds that are not capable of inhibiting the HMGCR enzyme cannot be considered statins, although their structure is similar to known statins.

As it is used herein, the term "hypocholesterolemic" refers to any pharmacologically active substance having the property of reducing blood cholesterol levels or cholesterol levels in other tissues.

As it is used herein, the term "nervous system or neurological disease" includes diseases that can affect the functioning of both the central nervous system, i.e., the spinal cord (myelopathy) or the brain (encephalopathy), and the peripheral nervous system, i.e., the nerves, and may cause movement difficulties, speech difficulties, learning difficulties, memory difficulties, difficulties in swallowing or changes in functioning of the senses or moods. The group of neurological diseases includes neurodegenerative and other diseases such as, for example, epilepsy, meningitis, strokes, spina bifida, polyneuropathies, vascular pathologies, etc.

As it is used herein, the term "neurodegenerative disease" includes diseases which result from the degeneration or deterioration of nervous tissue, particularly of neurons, leading over time to a dysfunction or to a disability; the term degeneration includes loss of cell viability, loss of cell function and/or loss of the number of cells (neurons or others). Illustrative, non-limiting examples of neurodegenerative diseases include Alzheimer's disease, Huntington's disease, Parkinson's disease, amyotrophic lateral sclerosis (ALS) or multiple sclerosis, Creutzfeldt-Jakob, Friedreich's ataxia, Lewy body dementia, spinal muscular atrophy, spongiform encephalopathies, Devic's disease, Guillain-Barré syndrome, Canavan disease, spondylosis, Lafora disease, Down syndrome, Korsakoff's syndrome, etc. In a particular embodiment, said neurodegenerative disease is a disease related to neuronal death caused by a substance which, for example, causes oxidative stress or endoplasmic reticulum stress or apoptosis or excitotoxicity or cytoskeleton disorganization or electron transport chain inhibition or protein hyperphosphorylation or dephosphorylation or neuronal death in general.

As it is used herein, the term "cognitive impairment" refers to the loss or alteration of mental functions, such as memory, orientation, language, visual recognition or conduct, which interfere with the social activity and interaction of the person affected persistently over time.

As it is used herein, the term "epilepsy" refers to a chronic brain syndrome having various causes, characterized by recurrent seizures due to excessive hypersynchronic discharges of nervous impulses by brain neurons, associated eventually with various clinical and paraclinical manifestations. The seizures can be convulsive or non-convulsive. Epilepsy can have many causes; in some cases it can be due to different types of brain injuries (e.g., brain traumas, sequelae of meningitis, tumors, etc.); in other cases there is no injury but a genetic predisposition to seizures; in other cases, the etiology of the epilepsy can be environmental, due to pharmacological treatments, due to excitotoxicity, trauma, stress processes, aging, development problems, neurological diseases, psychological crises, problems during gestation, problems during labor, etc.

As it is used herein, the term "epileptic or convulsant" refers to any epileptic seizure or convulsion of any etiology, for example, genetic, environmental, due to pharmacological treatments, due to excitotoxicity, due to trauma, due to stress processes, due to aging, due to development problems, due to neurological diseases, due to psychological crises, due to problems during gestation, due to problems during labor, etc. An epileptic seizure occurs when an abnormal electrical activity in the brain causes an involuntary change of body movement or function, feeling, in the capacity of being alert or in behavior, and can be partial or generalized (convulsive or non-convulsive).

As it is used herein, the term "subject" refers to a member of a mammal species and includes but is not limited to domestic animals, primates and humans; preferably, the subject is a male or female human being of any age or race. In a particular embodiment, said subject is a mammal which suffers, or is susceptible to suffering, pathological processes associated with age, such as aging, or a neurodegenerative disease, such as a chronic neurodegenerative disease.

As it is used herein, the term "pharmaceutically acceptable" refers to the fact that the compound is physiologically tolerable and generally does not cause an allergic reaction or a similar unfavorable reaction, such as a gastric disorder, dizziness or the like, when administered to a subject; said term "pharmaceutically acceptable" preferably means approved by a government regulatory agency or listed in the United States Pharmacopoeia or in another generally recognized pharmacopoeia for use in animals (e.g., European Pharmacopoeia, etc.).

As it is used herein, the term "pharmaceutically acceptable salt" includes "pharmaceutically acceptable metal salts" as well as "pharmaceutically acceptable amine salts". The term "pharmaceutically acceptable metal salt" contemplates salts formed with sodium, potassium, calcium, magnesium, aluminum, iron or zinc ions. The term "pharmaceutically acceptable amine salt" contemplates salts with ammonia and organic nitrogen bases strong enough to form salts with carboxylic acids. Said pharmaceutically acceptable salts can be obtained by conventional methods known by persons skilled in the art.

Due to the nature of compounds NST0076 and NST0078 of the invention, and taking into account that U.S. Pat. No. 654,151 B1 describes a methyl analog of simvastatin obtained by means of a structural modification in the β-hydroxypyranone ring of the molecule and having extraordinary HMGCR inhibiting capacity, the new compounds NST0076 and NST0078 would be expected to show high HMGCR inhibiting capacity. Surprisingly, and as shown in FIG. 1 of Example 2, the results indicate that none of the compounds was capable of efficiently inhibiting HMGCR. In fact, while NST0076 showed inhibition of the enzyme similar to monacolin J and much less than that of simvastatin (about 28 times less); NST0078 showed no inhibitory effect on the enzyme (about 1,900 times less than simvastatin).

Figure 2:
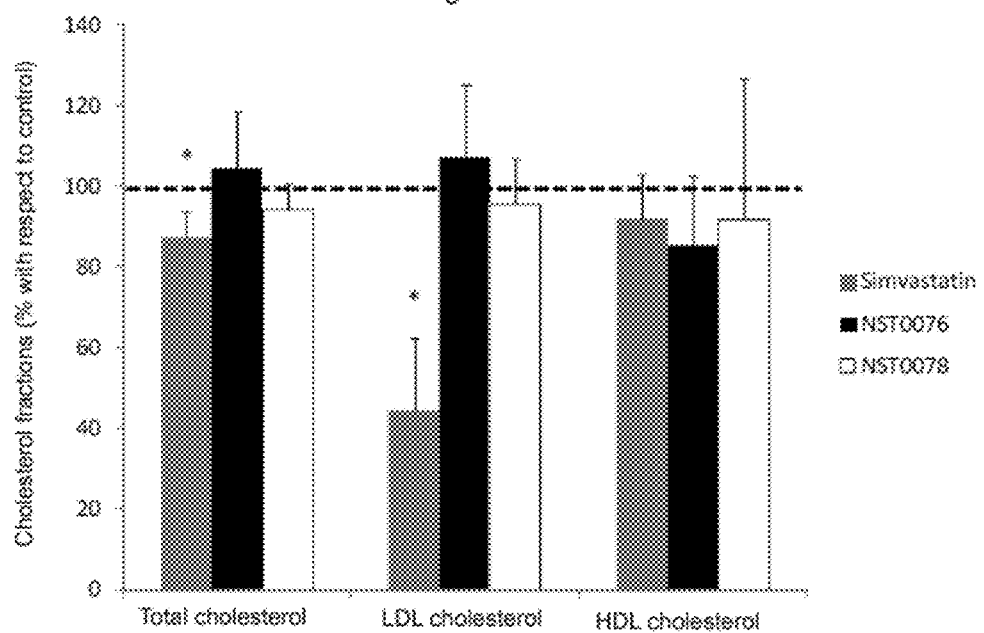
FIG. 2 is a bar graph depicting the hypocholesterolemic effect of simvastatin and of NST0076 and NST0078 12 h after i.p. administration of a suspension of each of the molecules at 50 mg/kg to male, apoB100 transgenic mice (n=4-5/group). Total cholesterol, LDL cholesterol and HDL cholesterol were quantified in the plasma of the rodents by means of enzymatic and spectrophotometric techniques. The results are the mean±SD of the change in cholesterol levels with respect to the control. * Significant difference with respect to the control group (vehicle), according to Student's t-test (p<0.05).

For the purpose of studying the effect of compounds NST0076 and NST0078 on cholesterol metabolism, the inventors decided to evaluate their cholesterol and cholesterol fraction level reducing capacity in vivo using a familial hyperlipidemia model in rodents. As shown in FIG. 2 of Example 2, compounds NST0076 and NST0078 do not show any hypocholesterolemic effect, unlike simvastatin which reduced plasma cholesterol levels, mainly at the LDL fraction level.

Subsequently, and even though the compounds did not have hypocholesterolemic properties, the inventors decided to evaluate the neuroprotective effect of NST0076 and NST0078 in vivo. To that end, the inventors used the administration of an excitotoxic substance to induce neuronal damage which caused convulsive seizures and epilepsy in animals. For this reason, the inventors decided to analyze if the compounds of this invention showed an antiepileptic and anticonvulsant effect with respect to the damage produced by an excitotoxic substance (Example 3, FIG. 3), and further determining if they protected against neuronal death and neuroinflammation caused by an excitotoxic substance (FIGS. 4 and 5), surprisingly finding that the administration of NST0076 and NST0078 reduced convulsive seizures, neuronal death and the associated neuroinflammation.

Figure 6:
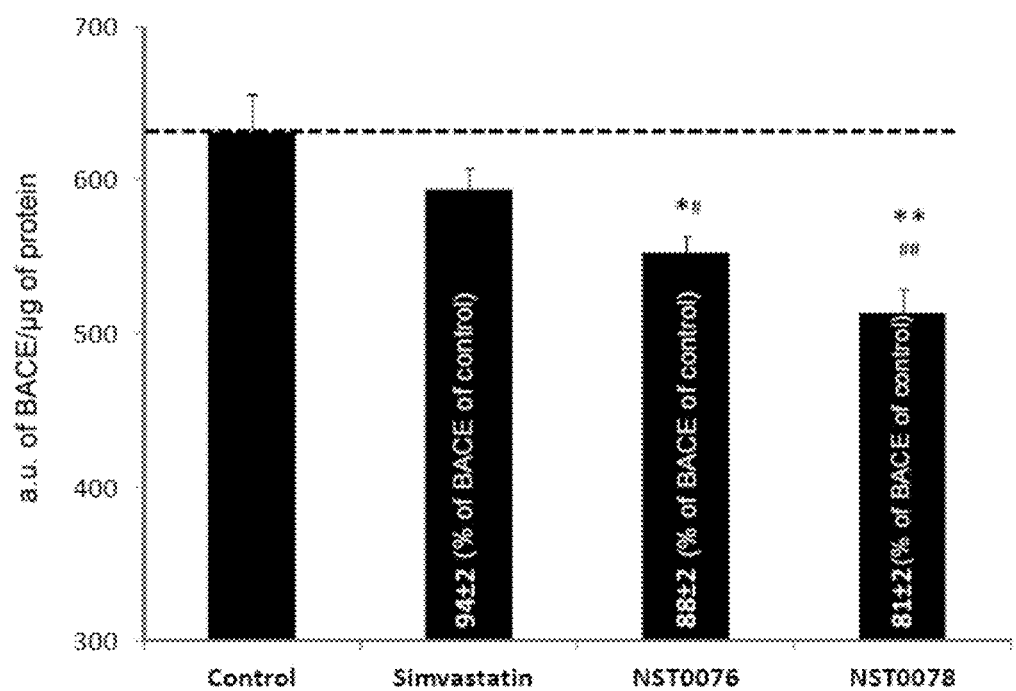
FIG. 6 is a bar graph depicting the mean±SEM of the β-secretase (BACE) enzymatic activity in the brain of mice 24 h after i.p. administration of 50 mg/kg of a suspension of simvastatin, NST0076, NST0078 or of the equivalent volume of the vehicle thereof (0.5% methylcellulose in saline solution) to male FVB mice. Enzymatic activity was determined in vitro in brain homogenates by means of using a fluorogenic substrate and was expressed in arbitrary units of the enzyme normalized by the amount of protein (determined by means of the BCA method). *p<0.05 with respect to the control group; **p<0.01 with respect to the control group; #p<0.05 with respect to the Simvastatin group; ##p<0.01 with respect to the Simvastatin group (Student's t-test test).

To demonstrate if the compounds had effects on APP metabolism, it was determined whether or not NST0076 and NST0078 were capable of modifying BACE activity in vivo. FIGS. 6 and 7 of Example 4 show that both in the brain of mice and in the brain of zebra fish both compounds have a higher potential than simvastatin for reducing BACE activity 24 h after administering same, so they can be used in diseases with impaired APP metabolism such as AD.

For the purpose of studying the blood-brain barrier (BBB) passage of compounds NST0076 and NST0078, different parameters such as theoretical BBB passage, percentage of passage and effective permeability (FIG. 8) were analyzed as described in Example 5. In the in vitro assay to determine BBB passage by passive diffusion (PAMPA method), compounds NST0076 and NST0078 showed a surprisingly high BBB passage greater than simvastatin (1.5 and 1.7 times more than simvastatin, respectively). Log BB (partition coefficient of the compound between plasma and brain tissue) values of NST0076 and NST0078 (0.19 and 0.27, respectively) were therefore greater than those of simvastatin (0.17), corroborating the results of the previous assay. The inventors then decided to study the degree of compound penetration in vivo, determining in the brain of mice the concentrations reached 1, 2, 4 and 6 h after administering the compounds intraperitoneally (i.p.) at 50 mg/kg, as shown in FIG. 9, Example 5. Compounds NST0076 and NST0078 showed a BBB passage surprisingly higher than simvastatin, with AUC values of 37 and 17 µg h/g, respectively, for NST0076 and NST0078 with respect to 12 µg h/g for simvastatin. Additionally, the authors decided to evaluate the plasma concentrations of the three compounds, as shown in FIG. 10, Example 5, observing that compounds NST0076 and NST0078 show plasma levels much higher than those of simvastatin at different points in time, with AUC values of 12 and 17 µg h/mL for NST0076 and NST0078, respectively, and of 0.7 µg h/mL for simvastatin.

The pharmaceutical composition provided by this invention can contain compounds NST0076 and/or NST0078 of the invention, and/or the hydroxy acid forms thereof and/or a pharmaceutically acceptable salt of said hydroxy acids and/or a pharmaceutically acceptable prodrug or solvate of the compound or of the hydroxy acid forms thereof, together with one or more pharmaceutically acceptable adjuvants, vehicles or excipients.

The term pharmaceutically acceptable "salt, prodrug or solvate" relates to any pharmaceutically acceptable salt, solvate or any other compound which is capable of providing (directly or indirectly) a compound as has been described in the present invention in its administration to the recipient. Nevertheless, pharmaceutically unacceptable salts also fall within the scope of the invention, since the latter can be useful for the preparation of pharmaceutically acceptable salts. The salts and prodrugs can be prepared by means of methods known in the state of the art.

Any compound which is a prodrug of the compounds of formula (I) or of the hydroxy acid forms thereof is within the scope of the invention. The term "prodrug" is used in its broadest meaning and encompasses those derivatives which are converted in vivo into the compounds of the invention. Such derivatives would be evident to a person having ordinary skill in the art and include the following derivatives of the present compounds: esters, amino acid esters, phosphate esters, metal sulfonate salt esters, carbamates and amides. The compounds according to the invention can be in crystalline form or as free compounds or as solvates (for example, hydrates) and it is intended that both forms are within the scope of the present invention. Solvation methods are generally known in the state of the art. In a particular embodiment, the solvate is a hydrate.

The pharmaceutical compositions containing compounds NST0076 or NST0078, or a hydroxy acid form thereof or a pharmaceutically acceptable salt of said hydroxy acids, can be formulated in any pharmaceutical dosage form suitable for administration by the chosen administration route, e.g., oral, parenteral (subcutaneous, intramuscular, intravenous, intraperitoneal, etc.), topical, rectal route, etc. By way of a non-limiting illustration, the pharmaceutical compositions provided by this invention can be formulated in a solid pharmaceutical dosage form administered by oral route (e.g., granules, tablets, capsules, etc.), in a liquid pharmaceutical dosage form administered by oral route (e.g., solutions, suspensions, emulsions, etc.), in a pharmaceutical dosage form administered by parenteral route (e.g., solutions, suspensions, emulsions, etc.). To that end, in each case, the suitable pharmaceutically acceptable vehicles and excipients will be chosen for the chosen pharmaceutical dosage form and route of administration, for example, binding agents, diluents, disintegrating agents, lubricants, wetting agents, etc., for the formulation of solid pharmaceutical dosage forms, and buffers, surfactants, etc., for the formulation of liquid pharmaceutical dosage forms. Said vehicles and excipients must be pharmaceutically acceptable and pharmacologically tolerable and have to be able to be combined with other components of the formulation without exerting any adverse effect on the treated subject. Information on said vehicles and excipients, as well as on said pharmaceutical dosage forms of said active ingredient, can be found in Galenic pharmacy treatises. A review of the different pharmaceutical dosage forms of drugs, in general, and of their methods of preparation can be found in the book "Tratado de Farmacia Galénica" ("by C. Fauli i Trillo, 1$^{st}$ Edition, 1993, Luzán 5, S. A. de Ediciones.

The pharmaceutical composition provided by this invention comprises compounds NST0076 and/or NST0078, and/or a hydroxy acid form thereof and/or a pharmaceutically acceptable salt of said hydroxy acids, in a therapeutically effective amount. In the sense used in this description, the expression "therapeutically effective amount" relates to the amount of compound calculated to cause the desired effect. The dose of compounds NST0076 and/or NST0078, and/or a hydroxy acid form thereof and/or a pharmaceutically acceptable salt of said hydroxy acids, to be administered to a subject can vary within a wide range depending on a number of factors, among which the characteristics of the compound used, e.g., its biological half-life and activity, the concentration of the compound in the pharmaceutical composition, the clinical presentation of the subject, the severity of the pathology, the chosen pharmaceutical dosage form, etc., are included. The pharmaceutical composition provided by this invention can be administered one or more times a day for preventive or therapeutic purposes or, alternatively, other administration regimens can be followed, not necessarily daily but also at precise times, weekly, etc.

If desired, the pharmaceutical composition provided by this invention can be used together with other drugs, for example, drugs useful in the treatment of neurodegenerative or neurological diseases, cognitive impairment, epilepsy, epileptic seizures or convulsions, or diseases with impaired APP metabolism, for the purpose of increasing the efficacy of the pharmaceutical composition provided by this invention, a combination therapy thus being generated. Said additional drugs can be part of the same pharmaceutical composition or, alternatively, can be provided as a separate pharmaceutical composition for administration at the same time (simultaneous administration) as the pharmaceutical composition provided by this invention or at different times (sequential administration) with respect to the administration of the pharmaceutical composition provided by this invention.

The following examples serve to illustrate the invention and must not be considered as limiting thereof.

Example 1

Synthesis of (1S,3R,7S,8S,8aR)-8-(2-((2R,4R)-4-hydroxy-5-methyl-6-oxo-tetrahydro-2H-pyran-2-yl)ethyl)-3,7-dimethyl-1,2,3,7,8,8a-hexahydro-naphthalen-1-yl 2-ethylbutanoate (NST0076) and (1S,3R,7S,8S,8aR)-8-(2-((2R,4R)-5-ethyl-4-hydroxy-6-oxo-tetrahydro-2H-pyran-2-yl)ethyl)-3,7-dimethyl-1,2,3,7,8,8a-hexahydronaphthalen-1-yl 2-ethylbutanoate (NST0078)

The compounds of the invention identified as NST0076 and NST0078 were prepared by means of direct alkylation of the lovastatin derivative, (1S,3R,7S,8S,8aR)-8-(2-((2R,4R)-4-hydroxy-6-tetrahydro-pyran-2-yl)ethyl)-3,7-dimethyl-1,2,3,7,8,8a-hexahydronaphthalen-1-yl 2-ethylbutanoate, identified as NST0037 in patent EP2241561 with the corresponding alkyl halide.

Preparation of Compound NST0076

The alkylation of NST0037 with MeI using LiHMDS in THF as base produced the desired product with a 29% yield.

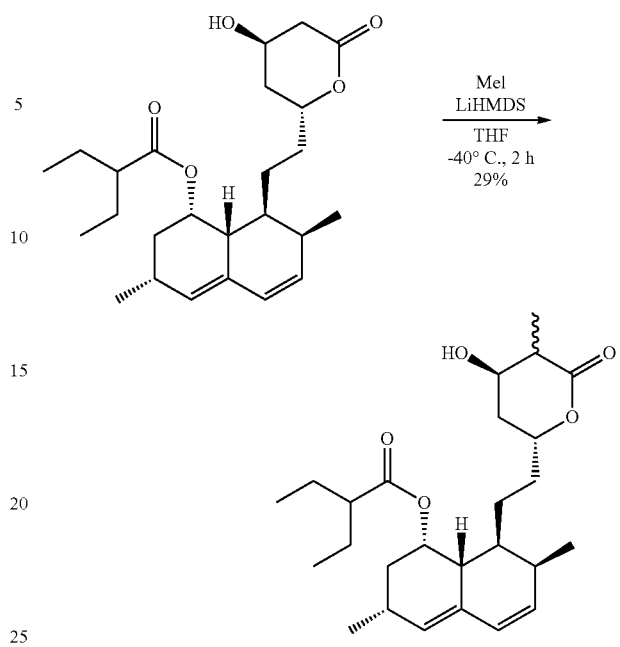

Specifically, the experimental phase was carried out as follows: a solution containing the starting substance (0.410 g, 0.980 mmol) in anhydrous THF (10 mL) is cooled at −40° C. and a 1 M solution of LiHMDS.THF (3.00 mL, 3.00 mmol) is added dropwise. The reaction mixture is stirred at this temperature for 30 min and MeI (0.090 mL, 1.44 mmol) is then added. The resulting orange solution is stirred at −40° C. for 2 hours. $H_2O$ (20 mL) is added and the phases are separated. The aqueous phase is extracted again with AcOEt (2×10 mL). The combined organic phases are washed with a 10% HCl solution (10 mL) and a saturated NaCl solution (10 mL). The resulting organic phase is dried with anh. $Na_2SO_4$, filtered and concentrated. An oil is obtained which is purified by means of silica gel chromatography (40% AcOEt/hexane) to provide a cream solid which is ground and washed with hexane (2×1 mL), 0.077 g of desired product being obtained (Rf=0.6 (50% AcOEt/hexane), white solid, 29% yield).

$^1$H-NMR (CDCl$_3$, 250 MHz) δ ppm: 6.00 (d, J=9.3 Hz, 1H), 5.92-5.72 (m, 1H), 5.49 (d, J=20.0 Hz, 2H), 4.60-4.37 (m, 1H), 4.00-3.77 (m, 1H), 2.72-1.43 (m, 22H), 1.32 (d, J=6.9 Hz, 3H), 1.09 (d, J=7.4 Hz, 3H), 1.02-0.81 (m, 6H).

Preparation of Compound NST0078

The alkylation of NST0037 with EtI using LiHMDS in anhydrous THF as base produced the desired product with a 14% yield.

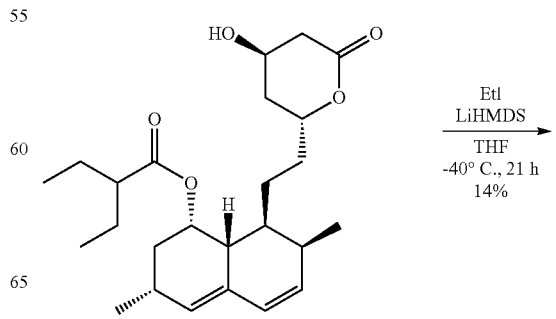

-continued

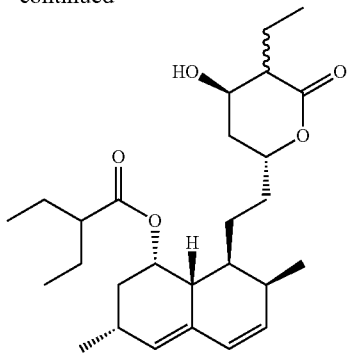

Specifically, the experimental phase was carried out as follows: a solution containing the starting substance (1.40 g, 3.35 mmol) in anhydrous THF (34 mL) is cooled at −40° C. and a 1 M solution of LiHMDS.THF (10.10 mL, 10.10 mmol) is added dropwise. The reaction mixture is stirred at this temperature for 40 min and EtI (0.397 mL, 5.01 mmol) is then added. The resulting orange solution is stirred at −40° C. for 21 hours. H$_2$O (50 mL) is added and the phases are separated. The aqueous phase is extracted again with AcOEt (2×30 mL). The combined organic phases are washed with a 10% HCl solution (50 mL) and a saturated NaCl solution (50 mL). The resulting organic phase is dried with anhydrous Na$_2$SO$_4$, filtered and concentrated. An oil is obtained which is purified by means of two silica gel chromatographies (10-60% AcOEt/hexane) and (70% Et$_2$O/hexane) to provide 0.125 g of the desired product (Rf=0.6 (50% AcOEt/hexane), white solid, 14% yield)

$^1$H-NMR (CDCl$_3$, 250 MHz) δ ppm: 6.00 (d, J=9.3 Hz, 1H), 5.86-5.73 (m, 1H), 5.49 (d, J=20.0 Hz, 2H), 4.55-4.41 (m, 1H), 4.06-3.94 (m, 1H), 2.54-1.15 (m, 20H), 1.14-1.01 (m, 6H), 0.94-0.80 (m, 10H).

Example 2

Study of the Hypocholesterolemic Effect of Compounds NST0076 and NST0078

2.1. Inhibition of 3-Hydroxy-3-Methylglutaryl Coenzyme A Reductase (HMGCR) Enzymatic Activity In Vitro by NST0076 and NST0078 with Respect to Simvastatin and Monacolin J The degree of inhibition of the HMGCR enzyme in vitro by NST0076 and NST0078 in the hydroxy acid form thereof was studied. The effect of these compounds was compared with that of a reference statin, i.e., simvastatin, also in the hydroxy acid form thereof, and with monacolin J.

During the reaction, HMGCR uses NADPH (Nicotinamide Adenine Dinucleotide Phosphate) as reducing agent and 3-hydroxy-3-methylglutaryl coenzyme A (HMG-CoA) as substrate. Mevalonic acid is obtained as a reaction product, and it serves as substrate for the subsequent reaction to continue with cholesterol synthesis. The enzymatic reaction object of study is schematized as follows:

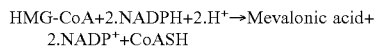

This in vitro assay is based on the spectrophotometric measurement of the decrease in absorbance at 340 nm, representing oxidation of NADPH by the catalytic subunit of HMGCR in the presence of the substrate. The assays include: (i) blank (without enzyme); (ii) control (without test compound); and (iii) test compounds: simvastatin, monacolin J, NST0076 and NST0078 at concentrations of 4, 10, 40, 100, 400, 800, 1 000, 4 000, 10 000, 40 000 and 80 000 nM assayed in duplicate after activation in 0.1 N NaOH. Briefly, the assay is performed in a 96-well plate with reaction buffer 50 mM KH$_2$PO$_4$, 1 M KCl, 2 mg/ml bovine serum albumin (BSA) and 5 mM DTT, at pH=7.3, and the concentrations of the reagents in the reaction mixture are 0.2 mM HMG-CoA, 3 µU/point HMGCR and 0.2 mM NADPH. The plate is read in a spectrophotometer at 340 nm and 37° C. The percentage of HMGCR enzymatic activity with respect to the control is calculated by measuring the decrease in absorbance at 340 nm 20 min after starting the reaction, and the IC$_{50}$ (concentration at which 50% of the enzymatic activity is inhibited) value is calculated by means of the Trimmed Spearman-Karber method (Version 1.5).

Surprisingly, as shown in FIG. 1 the results indicate that compounds NST0076 and NST0078 do not significantly inhibit the HMGCR enzyme [IC$_{50}$=603±177 nM for NST0076, whereas NST0078 was not capable of inhibiting the enzyme (IC$_{50}$ 40 µM)], unlike simvastatin which showed an IC$_{50}$=21±3 nM, so NST0076 has about 28 times less strength than simvastatin, similarly to what occurs with monacolin J, whereas NST0078 shows barely any inhibitory capacity.

2.2. Hypocholesterolemic Effect of NST0076 and NST0078 in an Endogenous (Familial) Hypercholesterolemia Model Based on the results of the preceding point, the inventors decided to evaluate the hypocholesterolemic capacity of the compounds in vivo.

To that end, adult, male transgenic ApoB100 mice (n=4-5/group) (Powell-Braxton L, Veniant M, Latvala R D, Hirano K I, Won W B et al. A mouse model of human familial hypercholesterolemia: markedly elevated low density lipoprotein cholesterol levels and severe atherosclerosis on a low-fat chow diet. Nat Med. 1998. 4: 934-938), which show a deficiency in removing cholesterol from blood, causing an abnormally high increase in plasma cholesterol, were used. The experiments were carried out by strictly following the Guidance on the Operation of Animals (Scientific Procedures, Act. 1986). The animals had their respective quarantine period and were treated with maximum precaution to minimize possible contaminations during inoculations and handling.

Compounds NST0076, NST0078 and simvastatin were prepared at 12.5 mg/mL, suspensions thereof being obtained. The mice were inoculated i.p. with 50 mg/kg of the compounds. Control mice were inoculated with equivalent volumes of the vehicle. Blood was drawn in fasting conditions before treating the animals and 12 h after treatments. Plasma, which was subsequently frozen, was obtained in both cases. The plasma total, LDL and HDL cholesterol concentration was quantified by enzymatic and spectrophotometric methods. After determining cholesterol levels and cholesterol fraction levels (baseline levels and 12 h after treatments), the change thereof with respect to the baseline level was calculated, and the results were depicted as a percentage with respect to the control group. FIG. 2 shows the changes in the different cholesterol fractions in the different treatment groups. The results indicate that only simvastatin produces statistically significant reductions in cholesterol mediated fundamentally by the reduction of LDL. Compounds NST0076 and NST0078 in turn did not show any hypocholesterolemic effect in this model.

Example 3

Antiepileptic and Neuroprotective Effect of NST0076 and NST0078 Against the Action of an Excitotoxic Substance in Mice 3.1. Protective Effect of NST0076 and NST0078 Against Epilepsy Caused by the Acute Administration of an Excitotoxic Substance in Mice Based on the previous results, the inventors decided to study the neuroprotective effect of the different compounds in a neuronal death model induced by the administration of an excitotoxic substance such as kainate to animals which in some cases induces epileptic seizures and convulsions. Furthermore, it has been demonstrated that pretreatment with simvastatin before administering kainate prevents the occurrence of said epileptic seizures and convulsions (Ramirez C, Tercero I, Pineda A, Burgos J S. Simvastatin is the statin that most efficiently protects against kainate-induced excitotoxicity and memory impairment. J Alzheimers Dis. 2001. 24: 161-174). As a result, the inventors decided to find out if molecules NST0076 and NST0078 showed the antiepileptic character observed for simvastatin, although they did not show a hypocholesterolemic effect in vivo and an inhibitory effect in vitro on HMGCR.

All the animals included for the experimental process were male mice 12 weeks of age from the FVB/NRj strain. The experiments were carried out strictly following the Guidance on the Operation of Animals (Scientific Procedures, Act. 1986). The animals had their respective quarantine period and were treated with maximum precaution to minimize possible contaminations during inoculations and handling.

The animals were divided into five groups: Vehicle group (n=9), Vehicle+KA group (n=10 animals); Simvastatin+KA group (n=12 animals); NST0076+KA group (n=10 animals); NST0078+KA group (n=10 animals). All the treatments were prepared in the vehicle, i.e., 0.5% methylcellulose in saline solution. 24 h and 0.5 h before administering kainate, the mice from the different groups were inoculated intraperitoneally with their respective treatment at a dose of 3.125 mg/kg, except the control groups which were treated only with the vehicle. After the intraperitoneal inoculation of 100 µL of kainate dissolved in PBS at a dose of 23 mg/kg, the animals were individually housed in enclosures for follow-up. During observation, the maximum level of epilepsy in the animals was recorded according to the Racine scale every ten minutes for 120 minutes post-inoculation (m.p.i.). The maximum level of epilepsy reached by each of the mice in the different time intervals into which the 120 minutes of observation were divided was depicted and the resulting area under the curve (AUC) was determined for each mouse. The results are the mean±SEM of the percentage of the AUC with respect to the Vehicle+KA group.

Figure 3:
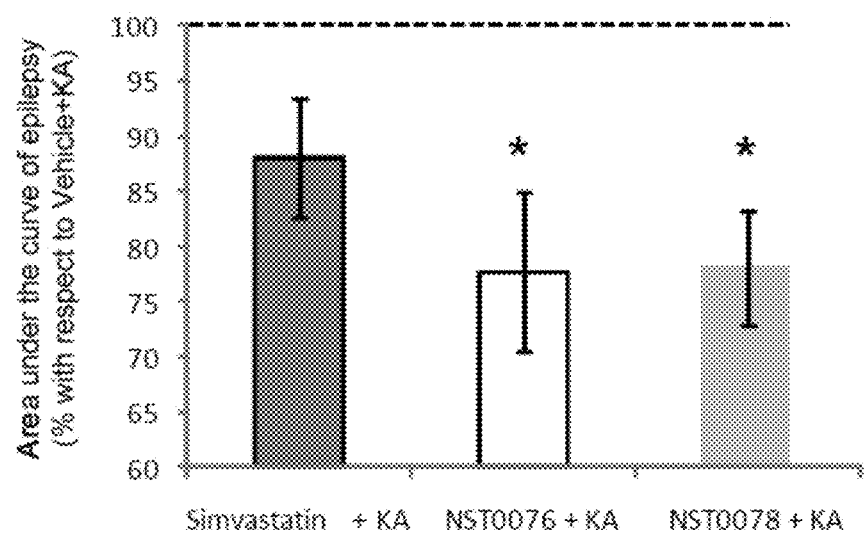
FIGS. 3, 4 and 5 show the degree of protection by the compounds in an in vivo model of excitotoxic damage in mice.

FIG. 3 shows that the pretreatment of mice with NST0076 and NST0078 caused greater reduction of the levels of epilepsy compared to simvastatin, and furthermore it is statistically significant (*p-value<0.05; Student's t-test), showing the antiepileptic potential of the compounds.

3.2. Protective Effect of NST0076 and NST0078 Against Neuronal Death Caused by the Acute Administration of an Excitotoxic Substance in the Hippocampus of Mice Based on the results of protection shown by NST0076 and NST0078 against epileptic syndromes and convulsions generated by an excitotoxic substance, the inventors decided to find out if said protective effect was associated with the reduction of neuronal death caused by kainate in the hippocampus of mice. The animals were divided into five groups: Vehicle+PBS+KA group (n=9), Vehicle+KA+Vehicle group (n=20 animals); Simvastatin+KA+Simvastatin group (n=12 animals); NST0076+KA+NST0076 group (n=10 animals); NST0078+KA+NST0078 group (n=10 animals). All the treatments were prepared in the vehicle, i.e., 0.5% methylcellulose in physiological saline. 24 h and 0.5 h before administering kainate, the mice from the different groups were inoculated intraperitoneally with their respective treatment at a dose of 3.125 mg/kg, except the control groups which were treated only with the vehicle. Damage was induced by means of an intraperitoneal injection of kainate dissolved in PBS at a dose of 23 mg/kg. The Vehicle+PBS+Vehicle group received equivalent volumes of PBS. The treatment continued to be administered for three days after the inoculation of kainate (1 dose/day). In all cases, one day after the last treatment the mice were sacrificed and their brains were extracted, fixed and included in paraffin. Coronal sections of the brain that were 5 µm thick were prepared and stained with hematoxylin and eosin (H&E) for analyzing the neurons of the hippocampus.

Figure 4:
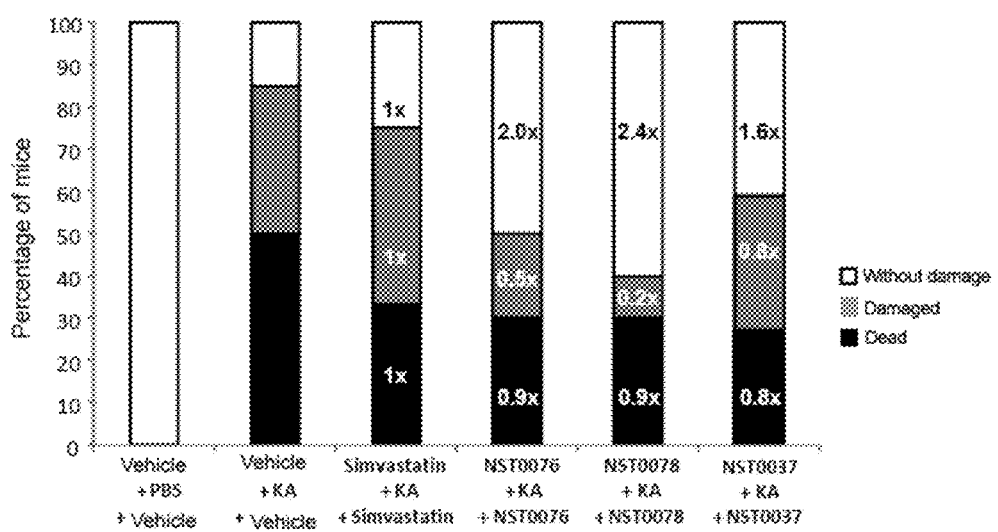

The percentage of animals that did not survive the administration of KA (dead animals), the percentage of animals that showed neurons in apoptosis or dead neurons (damaged animals) and the percentage of animals without any type of damage (animals without damage) was determined for each of the groups. As seen in FIG. 4, the administration of kainate and treatment with vehicle caused the death of 50% of the animals and damage in the neurons of the hippocampus (fundamentally in the CA1, CA3 and dentate gyrus regions) in 35% of the mice, leaving 15% of the animals without any damages. In contrast, none of the mice treated with the vehicle and PBS showed any damage. Treatment with simvastatin in turn slightly reduced damage associated with KA (25% of the mice did not suffer any damage). However, surprisingly, treatment with NST0076 exceptionally increased the percentage of mice without any detected damage (50%), and particularly treatment with NST0078 increased the percentage of animals without damage up to 60%. These results demonstrate the differential neuroprotective character of molecules NST0076 and NST0078 with respect to simvastatin.

3.3. Protective Effect of NST0076 and NST0078 Against Brain Inflammation Induced by an Excitotoxic Substance Based on the results of protection shown by compounds NST0076 and NST0078 against neuronal death generated by kainate, the inventors decided to find out if said protective effect was associated with the reduction of reactive astrogliosis, and therefore if they played a role in induced neuroinflammation.

Based on the coronal sections of the brain obtained during the experiment described above, astrogliosis was analyzed by means of bright field immunohistochemistry for the glial fibrillary acidic protein (GFAP) in surviving animals.

Figure 5:
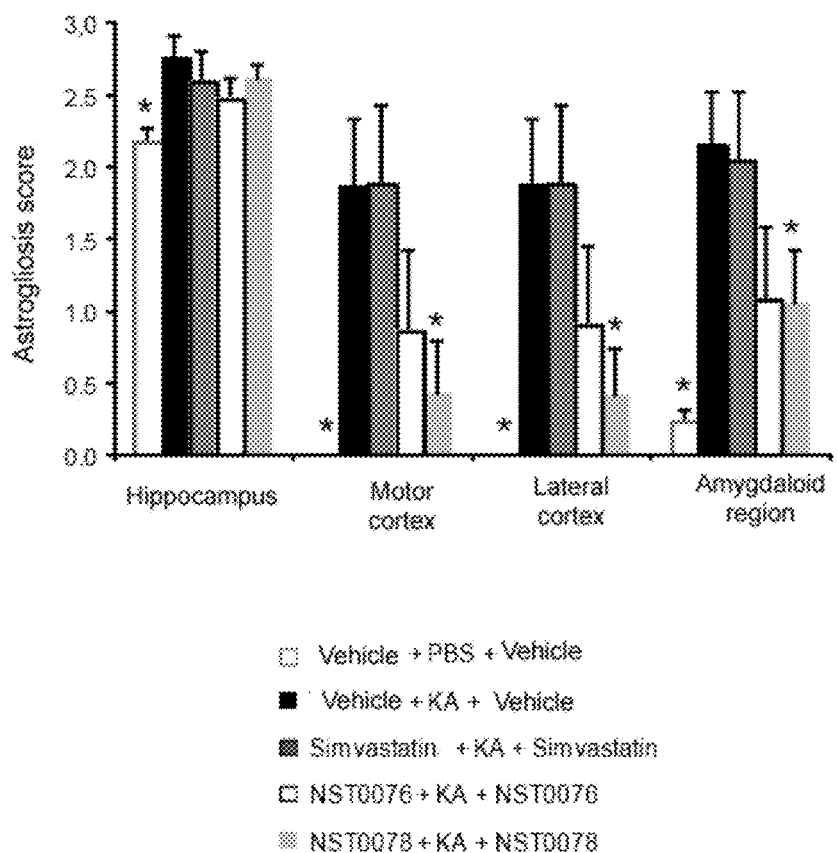

The degree to which astrogliosis has spread (or score) was determined on a scale of intensity from 0 to 3, where zero indicates the absence of reactive astroglia and three indicates maximum reactive astroglia, for each of the groups. As seen in FIG. 5, the administration of kainate caused the occurrence of reactive astroglia in a statistically significant manner in comparison with control mice (to which KA was not administered) in the regions of the brain that are most sensitive to KA (hippocampus, motor cortex, lateral cortex and amygdaloid region). Said figure also shows that treatment with simvastatin at the administered dose did not reduce the degree of astrogliosis induced by kainate. However, both NST0076 and NST0078 protected against astrogliosis induced by kainate in all the studied regions, said reduction being statistically significant in the case of treatment with NST0078 in the motor cortex and lateral cortex and in the amygdaloid region. These results confirm the neuroprotective character and also indicate the anti-inflammatory character of molecules NST0076 and NST0078.

Example 4

Inhibitory Effect on β-Secretase (BACE) Activity In Vivo 4.1. Inhibition of β-Secretase (BACE) Enzymatic Activity in the Brain of Mice by NST0076 and NST0078 with Respect to Simvastatin 24 h after i.p. Administration of 50 mg/kg Since the effect of the compounds on neuronal death had been demonstrated, the inventors decided to evaluate the possible effects of the molecules on mechanisms that are closely related to AD, and specifically, they studied their modulation of impaired β-amyloid precursor protein (APP) metabolism. For this reason, the effect of NST0076 and NST0078 on BACE in comparison with simvastatin was evaluated in the brains of wildtype mice. BACE is a key enzyme in AD because it produces Aβ plaques in the brain, a histopathological marker characteristic of the disease, by processing APP.

During the reaction, contacting a BACE-specific, fluorogenic substrate with a brain homogenate in which the enzyme is present allows quantifying the enzyme activity by means of measuring the fluorescence emitted.

The compounds object of study were prepared at 12.5 mg/mL in 0.5% methylcellulose in physiological saline, homogeneous suspensions thereof being obtained. Female FVB mice 4 months of age were treated i.p. with 50 mg/kg of the compounds or with equivalent volumes of the vehicle (n=6 mice/group). After 24 h, the animals were sacrificed and the brain was extracted and frozen at −20° C., first disposing of the cerebellum. After freezing the brains for 24 h, they were homogenized by making a 1/100 dilution in 0.1 M sodium acetate at pH 4. The samples were incubated for 10 minutes under cold conditions to favor lysis and to obtain the extract after centrifuging at 10,000 g for 10 minutes. The enzymatic reaction was then carried out. 50 μL of the samples were loaded in a flat bottom 96-well plate in duplicate, in addition to a blank (0.1 M sodium acetate at pH 4), a positive control (SK-N-MC cell extract) and a control including a specific inhibitor of the enzyme at 10 μM, all of this also in duplicate. 50 μL of a 20 μM fluorogenic BACE substrate (Mca-RPPGFSAFK) were added to the samples and controls, the final concentration in the well being 10 μM and the total reaction volume being 100 μL. After incubating the plate for 3 h in the dark at 37° C., fluorescence at an excitation wavelength of 320 nm and at an emission wavelength of 405 nm was recorded. The results obtained in arbitrary units were normalized by the amount of protein that was determined by the bicinchoninic acid (BCA) method.

FIG. 6 shows that compounds NST0076 and NST0078 were capable of reducing BACE enzymatic activity in a statistically significant manner, unlike simvastatin. Inhibition by NST0078 was greater even with respect to that shown by the specific inhibitor in vitro (85±4% of BACE activity with respect to the control).

4.2. Inhibition of β-Secretase (BACE) Enzymatic Activity in the Brain of Zebra Fish by NST0076 and NST0078 with Respect to Simvastatin 24 h after i.p. Administration of 100 mg/kg Since compounds NST0076 and NST0078 showed an inhibitory effect on BACE in mice, the inventors decided to evaluate the effect in a different animal species, for which purpose the assay was carried out in zebra fish. To that end, they evaluated the effect of compounds NST0076 and NST0078 on BACE in the brain of wildtype zebra fish with respect to simvastatin.

The compounds object of study were prepared at different concentrations according to the weight of the animals in 0.5% methylcellulose in physiological saline, homogeneous suspensions thereof being obtained. Female zebra fish 24 months of age were treated i.p. with 100 mg/kg of the compounds or with equivalent volumes of the vehicle (n=8 fish/group). After 24 h, the animals were sacrificed and the brain was extracted and frozen at −20° C. After freezing the brains for 24 h, they were homogenized in 500 μL of 0.1 M sodium acetate at pH 4. The samples were incubated for 10 minutes under cold conditions to favor lysis and to obtain the extract after centrifuging at 10,000 g for 10 minutes. The enzymatic reaction was then carried out in the same way as in the case mice.

FIG. 7 shows that compound NST0078 was capable of reducing BACE enzymatic activity with respect to the control in a statistically significant manner. However, this inhibitory effect was not observed in the brains of fish treated with simvastatin. These results show how compound NST0078 improves the effect of simvastatin on BACE enzymatic activity.

Example 5

Prediction of the Blood-Brain Barrier Passage of NST0076 and NST0078 with Respect to Simvastatin 5.1. Blood-Brain Barrier Passage of NST0076 and NST0078 with Respect to Simvastatin in an In Vitro Assay The in vitro blood-brain barrier (BBB) passage for compounds NST0076 and NST0078 in the hydroxy acid forms thereof was studied by means of the PAMPA (Parallel Artificial Membrane Permeability Assay) assay that mimics the BBB by means of a system including a mixture of brain lipids very similar to that existing in human BBB (Di L, Kerns E H, Fan K, McConnell O J, Carter G T. High throughput artificial membrane permeability assay for blood-brain barrier. Eur J Med Chem. 2003. 38 (3): 223-232). The passage of these compounds was compared with that of simvastatin hydroxy acid.

Compounds NST0076, NST0078 and simvastatin were assayed and verapamil, a compound with high permeability, was used as a positive control, whereas theophylline, a compound that does not cross the BBB, was used as a negative control.

According to the results obtained from $P_e$, barrier passage can be classified as:
$P_e > 4 \times 10^{-6}$ cm/s: high permeability for BBB passage
$P_e < 2 \times 10^{-6}$ cm/s: low permeability for BBB passage
$P_e$ 2-4×10$^{-6}$ cm/s: permeability for BBB passage inconclusive As shown in FIG. 8, the obtained results indicate that compounds NST0076 ($P_e = 6.12 \pm 0.99 \times 10^{-6}$ cm/s and 47±6% BBB passage) and NST0078 ($P_e = 7.28 \pm 2.24 \times 10^{-6}$ cm/s and 53±11% BBB passage) surprisingly show greater permeability for the BBB in vitro than simvastatin ($P_e$=4.2±0.3× $10^{-6}$ cm/s and 35±2% BBB passage). As shown in FIG. 8, the control passing the BBB (verapamil) and the control not passing the BBB (theophylline) behave suitably.

5.2. Theoretical Blood-Brain Barrier Passage of NST0076 and NST0078 with Respect to Simvastatin by Means of in Silico Analysis.

Based on the previous results, the inventors decided to study the blood-brain barrier (BBB) passage of compounds NST0076 and NST0078 using the Rishton theoretical approach (Rishton G M, LaBonte K, Williams A J, Kassam K, Kolovanov E. Computational approaches to the prediction of blood-brain barrier permeability: A comparative analysis of central nervous system drugs versus secretase inhibitors for Alzheimer's disease. 2006: 9 (3): 303-313).

The Rishton equation was used for determining the theoretical barrier passage since this formula takes into account c Log P (octanol/water partition coefficient) and PSA (polar surface area) parameters to obtain the log BB value which is defined as the partition coefficient of the compound between plasma and brain tissue. The calculation of said parameter for compounds NST0076 and NST0078 was 0.19 and 0.27, respectively, values which were surprisingly greater than those of simvastatin (0.17), which indicates that the three compounds theoretically cross the barrier (values between 0 and 0.5 would indicate barrier passage), compound NST0078 showing the highest permeability.

5.3. Blood-Brain Barrier Passage of NST0076 and NST0078 with Respect to Simvastatin In Vivo Based on the previous results, the inventors decided to study the concentrations reached by NST0076 and NST0078 in the brain after administration in mice. The compounds object of study were prepared at 12.5 mg/mL in 0.5% methylcellulose in physiological saline, homogeneous suspensions thereof being obtained. Male FVB mice 4 months of age were treated i.p. with 50 mg/kg of the compounds (n=4-8 mice/group/time). The animals were sacrificed 1, 2, 4 and 6 h after treatment by means of injecting Eutanax, the blood and brain being extracted after perfusion with PBS. The plasma obtained from the blood and the entire brain were frozen at −20° C. until analysis. The compounds were extracted from the tissues with ethyl acetate and resuspended in ethanol for subsequent UPLC-MS quantification. Fluvastatin was used as an internal standard.

FIG. 9 shows the concentrations reached by the different compounds in the lactone form in the brain at the different points in time that were analyzed, NST0076 and NST0078 having AUC and Cmax values surprisingly greater than those of simvastatin (and statistically significant for compound NST0076). Additionally, the concentrations of the lactone forms of compounds NST0076, NST0078 and simvastatin were evaluated in the plasma samples from the same mice, observing that compounds NST0076 and NST0078 have plasma levels considerably greater than simvastatin, as shown in FIG. 10.

What is claimed is:

1. A compound of formula (I), wherein R is selected from a methyl group and an ethyl group:

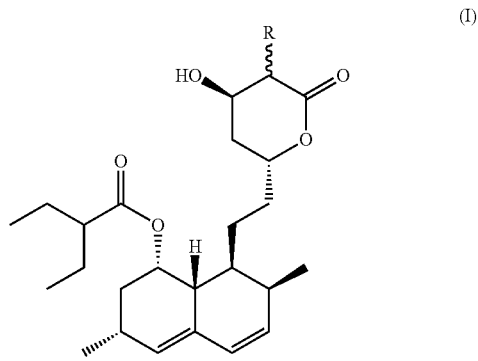

(I)

a hydroxy acid form thereof, a pharmaceutically acceptable salt of said hydroxy acid form, and a pharmaceutically acceptable prodrug and solvate of said compound and of the hydroxy acid form thereof.

2. The compound of formula (I) according to claim 1, wherein R is methyl.

3. The compound of formula (I) according to claim 1, wherein R is ethyl.

4. A pharmaceutical composition comprising:
one or more selected from the group consisting of the compound of formula (I) according to claim 1, a hydroxy acid form thereof, a pharmaceutically acceptable salt of said hydroxy acid form, and a pharmaceutically acceptable prodrug or solvate of the compound or of the hydroxy acid form thereof; and
at least one selected from the group consisting of a pharmaceutically acceptable adjuvant, carrier and vehicle.

\* \* \* \* \*